United States Patent
Galey et al.

[11] Patent Number: 6,156,899
[45] Date of Patent: Dec. 5, 2000

[54] N-ARYL-2-HYDROXYALKYLAMIDO COMPOSITIONS FOR INDUCING/STIMULATING HAIR GROWTH AND/OR RETARDING HAIR LOSS AND/OR FOR TREATING HYPERSEBORRHEA AND/OR ACNE

[75] Inventors: Jean-Baptiste Galey, Aulnay-Sous-Bois; Odile Destree, Villeparisis; Lionel Breton, Versailles, all of France

[73] Assignee: Societe L'Oreal S.A., Paris, France

[21] Appl. No.: 09/190,300

[22] Filed: Nov. 13, 1998

[30] Foreign Application Priority Data

Nov. 13, 1997 [FR] France ................................. 97 14241

[51] Int. Cl.⁷ .................................................. C07D 211/30
[52] U.S. Cl. ..................... 546/225; 546/247; 548/538; 548/542; 554/103; 554/106; 564/45; 564/48
[58] Field of Search ................... 546/225, 247; 548/538, 542; 564/45, 48; 554/103, 106

[56] References Cited

FOREIGN PATENT DOCUMENTS 0524781  1/1993  European Pat. Off. .
97/32562  9/1997  WIPO .

OTHER PUBLICATIONS

Chem. abstr. of JP–48096723, 1972.

*Primary Examiner*—Deborah D. Carr
*Attorney, Agent, or Firm*—Burns, Doane, Swecker & Mathis, L.L.P.

[57] ABSTRACT

Novel N-aryl-2-hydroxyalkylamido compounds having the formula (I):

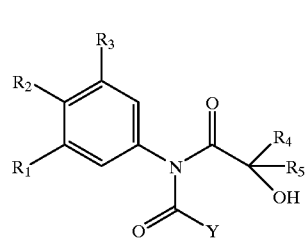

are well suited for inducing/stimulating hair growth and/or retarding hair loss and/or for therapeutically treating hyperseborrhea and/or acne.

42 Claims, No Drawings

N-ARYL-2-HYDROXYALKYLAMIDO COMPOSITIONS FOR INDUCING/STIMULATING HAIR GROWTH AND/OR RETARDING HAIR LOSS AND/OR FOR TREATING HYPERSEBORRHEA AND/OR ACNE

CROSS-REFERENCE TO PRIORITY APPLICATION

This application claims priority under 35 U.S.C. §119 of FR-97/14241, filed Nov. 13, 1997, assigned to the assignee hereof and hereby expressly incorporated by reference.

BACKGROUND OF THE INVENTION

1. Technical Field of the Invention

The present invention relates to novel N-aryl-2-hydroxyalkylamide compounds, to a process for the synthesis thereof, and to the formulation of at least one of said novel compounds into cosmetic/therapeutic compositions well suited for inducing and/or stimulating hair growth and/or retarding hair loss and/or for treating hyperseborrhoea and/or acne.

2. Description of the Prior Art

In human subjects the growth of the hair and its renewal are principally determined by the activity of the hair follicles. This activity is cyclical and essentially comprises three phases, namely, the anagen phase, the catagen phase and the telogen phase.

The active anagen phase, or growth phase, which lasts for several years and during which the hairs lengthen, is succeeded by a very short and transitory catagen phase, which lasts for a few weeks, and then by a resting or quiescent phase, also designated the telogen phase, which lasts for a few months.

At the end of the rest period, the hairs fall out and another cycle begins anew. The head of hair is thus continuously renewed and, out of the approximately 150,000 hairs on a human head, at each instant approximately 10% of them are at rest in the telogen phase and will thus be replaced in a few months.

However, various causes and challenges can result in a significant, temporary or definitive, loss of hair. Alopecia is essentially due to a disruption in hair renewal which initially gives rise to an acceleration of the frequency of the cycles at the expense of the quality of the hairs and then of their quantity. A progressive thinning of the head of hair takes place by regression of the so-called "terminal" hairs to the down stage. Certain regions are preferentially affected, in particular the temporal or frontal bulbs in man and, in woman, a diffuse alopecia of the vertex is observed.

By the term "alopecia" is intended an entire family of conditions of the hair follicle having as final consequence the partial or general definitive loss of the hair.

In a significant number of cases, early hair loss occurs in subjects who are genetically predisposed and it affects men in particular. It is more particularly androgenetic or androgenic alopecia or, alternatively, androgeno-genetic alopecia.

Compositions that eliminate or reduce the effects of alopecia and, in particular, that induce or stimulate hair growth or decrease hair loss have long been considered desiderata in the cosmetic and pharmaceutical industries.

In this regard, a large number of very diverse active compounds have been suggested for such purposes, for example, 2,4-diamino-6-piperidinopyrimidine 3-oxide or "Minoxidil" described in U.S. Pat. Nos. 4,139,619 and 4,596,812 or numerous derivatives thereof, such as those described, for example, in EP-0,353,123, EP-0,356,271, EP-0,408,442, EP-0,522,964, EP-0,420,707, EP-0,459,890 and EP-0,519,819.

SUMMARY OF THE INVENTION

A major object of the present invention is the provision of yet other such valuable active compounds, particularly those species that are potentially more active and/or less toxic.

Briefly, the present invention features novel N-aryl-2-hydroxyalkylamido compounds having the general formula (I):

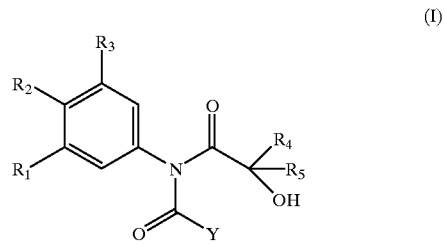

in which $R_1$ is a hydrogen atom, a halogen atom, a cyano group (—CN), a $C_1$–$C_4$ alkyl radical, a perfluoroalkyl radical or an —$OR_6$ radical, wherein $R_6$ is a hydrogen atom or a $C_1$–$C_4$ alkyl radical; $R_2$ is a nitro group (—$NO_2$), a cyano group (—CN), a halogen atom, an —$SO_2R_7$ radical, a —$COR_7$ radical or a —$COOR_7$ radical, wherein $R_7$ is a hydrogen atom, a $C_1$–$C_4$ alkyl radical or a phenyl radical optionally substituted by at least one halogen atom; $R_3$ is a hydrogen atom, a halogen atom, a cyano group (—CN), a $C_1$–$C_4$ alkyl radical optionally substituted by at least one halogen atom, or an —$OR_6$ radical, wherein $R_6$ is a hydrogen atom or a $C_1$–$C_4$ alkyl radical; $R_4$ is a hydrogen atom or a $C_1$–$C_4$ alkyl radical optionally substituted by at least one halogen atom; $R_5$ is a $C_1$–$C_4$ alkyl radical substituted by at least one halogen atom or a phenyl radical optionally substituted by at least one halogen atom, a cyano group (—CN) or a nitro group (—$NO_2$); Y is an —OR radical or an —NRR' radical; and R and R', which may be identical or different, are each a hydrogen atom, a $C_1$–$C_8$ alkyl radical optionally substituted by at least one hydroxyl radical (—OH), or a —$COOR_6$ radical; with the proviso that, when Y is —NRR', R and R', together with the nitrogen atom from which they depend, can form a 5- or 6-membered heterocyclic ring member.

DETAILED DESCRIPTION OF BEST MODE AND SPECIFIC/PREFERRED EMBODIMENTS OF THE INVENTION

More particularly according to the present invention, also featured are the optical and/or geometrical isomers of the subject novel compounds, alone or in admixture in all proportions, as well as the acylated derivatives or the pharmaceutically acceptable salts thereof.

Among the halogen atom substituents of the formula (I) compounds, preferred are fluorine, chlorine, iodine or bromine and, more preferably, fluorine.

By "$C_1$–$C_4$ alkyl radical" preferably are intended the acyclic radicals originating from the removal of a hydrogen atom from the molecule of a linear or branched hydrocarbon having from 1 to 4 carbon atoms and, in particular, the methyl, ethyl, propyl, isopropyl, butyl, isobutyl or tert-butyl radicals and, more particularly, the methyl radical.

By "alkyl radical optionally substituted by at least one halogen atom" are preferably intended the radicals defined above in which at least one hydrogen atom is substituted by a halogen atom, including the perhalogenated radicals in which all of the hydrogen atoms are replaced by an equal number of halogen atoms.

The "alkyl radicals substituted by at least one halogen atom" are preferably substituted by at least one chlorine or fluorine atom. The perhalogenated radicals are preferably perfluorinated radicals, in particular perfluoromethyl radicals.

When $R_1$ is a halogen atom, $R_1$ is preferably a chlorine atom.

When $R_1$ is a $C_1$–$C_4$ alkyl radical, $R_1$ is preferably a methyl radical.

When $R_1$ is a perfluoroalkyl radical, $R_1$ is preferably a trifluoromethyl radical (—$CF_3$).

When $R_1$ is an —$OR_6$ radical, $R_1$ is preferably a methoxy radical (—$OCH_3$).

When $R_2$ is a halogen atom, $R_2$ is preferably a chlorine atom.

When $R_2$ is an —$SO_2R_7$ radical, $R_7$ is preferably a phenyl radical.

When $R_2$ is a —$COR_7$ radical, $R_7$ is preferably a phenyl radical.

When $R_2$ is a —$COOR_7$ radical, $R_7$ is preferably an ethyl radical.

When $R_3$ is a halogen atom, $R_3$ is preferably a chlorine atom.

When $R_3$ is a $C_1$–$C_4$ alkyl radical optionally substituted by at least one halogen atom, $R_3$ is preferably a trifluoromethyl radical (—$CF_3$).

When $R_3$ is an —$OR_6$ radical, $R_6$ is preferably a methyl radical (—$CH_3$).

When $R_4$ is a $C_1$–$C_4$ alkyl radical, $R_4$ is preferably a methyl radical (—$CH_3$).

When $R_4$ is a $C_1$–$C_4$ alkyl radical substituted by at least one halogen atom, $R_4$ is preferably a trifluoromethyl radical (—$CF_3$).

When $R_5$ is a $C_1$–$C_4$ alkyl radical substituted by at least one halogen atom, $R_5$ is preferably a trifluoromethyl radical (—$CF_3$).

$R_4$ and $R_5$ can be identical but $R_4$ and $R_5$ preferably are different.

Y preferably represents an —NHR radical.

When R represents a $C_1$–$C_8$ radical, R is preferably a butyl radical.

When R represents a —$COOR_6$ radical, $R_6$ is preferably a propyl radical.

Exemplary compounds of formula (I) include:

(4-cyano-3-(trifluoromethyl)phenyl)-(3,3,3-trifluoro-2-hydroxy-2-methylpropionyl)carbamic acid;

the ethyl ester of (4-cyano-3-(trifluoro-methyl)phenyl)(3,3,3-trifluoro-2-hydroxy-2-methylpropionyl)carbamic acid;

1-(3,4-dichlorophenyl)-3-propyl-1-(3,3,3-trifluoro-2-hydroxy-2-methylpropionyl)urea;

1-(3,4-dichlorophenyl)-3-benzyl-1-(3,3,3-trifluoro-2-hydroxy-2-methylpropionyl)urea;

1-(3,4-dichlorophenyl)-3-piperidinyl-1-(3,3,3-trifluoro-2-hydroxy-2-methylpropionyl)urea;

1-(4-sulfonylphenyl)-3-propyl-1-(3,3,3-trifluoro-2-hydroxy-2-methylpropionyl)urea;

1-(4-benzoylphenyl)-3-propyl-1-(3,3,3-trifluoro-2-hydroxy-2-methylpropionyl)urea;

the ethyl ester of (3,4-dichlorophenyl)(3,3,3-trifluoro-2-hydroxy-2-methylpropionyl)carbamic acid;

1-(3,4-dichlorophenyl)-3-(4-hydroxybutyl)-1-(3,3,3-trifluoro-2-hydroxy-2-methylpropionyl)urea.

More particularly preferred are:

(4-cyano-3-(trifluoromethyl)phenyl)-(3,3,3-trifluoro-2-hydroxy-2-methylpropionyl)carbamic acid;

the ethyl ester of (4-cyano-3-(trifluoromethyl)phenyl)(3,3,3-trifluoro-2-hydroxy-2-methylpropionyl)carbamic acid;

1-(3,4-dichlorophenyl)-3-propyl-1-(3,3,3-trifluoro-2-hydroxy-2-methylpropionyl)urea.

This invention also features a process for the preparation of the compounds of formula (I).

This process is characterized in that, in a first stage, an N-aryl-2,4-dioxooxazolidine derivative is prepared, according to the technique described by Patton, T. L., *J. Org. Chem.*, 32(2), 383–388 (1967), by reacting an isocyanate with a cyanohydrin in an anhydrous solvent in the presence of an amine. The mixture obtained is treated in the presence of hydrochloric acid and then the N-aryl-2,4-dioxooxazolidine derivative formed is extracted using an organic solvent and then dried and purified by chromatography on a silica column. In a second stage, an excess of alcohol or of amine is added to a solution of N-aryl-2,4-dioxooxazolidine obtained in the first stage. The solution is heated to a temperature of from 25° C. to 70° C. for 1 to 7 days and then evaporated to dryness. The residue is purified by chromatography on a silica column or recrystallized.

Specific examples of the preparation of the compounds according to the invention are set forth in the examples to follow.

The present invention also features cosmetic or pharmaceutical compositions, particularly dermatological compositions, which comprise an effective amount of at least one of the compounds of formula (I).

Of course, the compositions according to the invention can comprise the compounds of formula (I) alone or in admixture in all proportions.

The amount of the compounds of formula (I) present in the compositions of the invention is, of course, a function of the desired effect and can thus vary to a great extent.

To provide an order of magnitude, if the composition is a cosmetic composition, it advantageously comprises at least one compound of formula (I) in an amount ranging from 0.0001% to 5% of the total weight of the composition and, preferably, in an amount ranging from 0.001% to 2% of the total weight of the composition.

To also provide another order of magnitude, if the composition is a pharmaceutical composition, it advantageously comprises at least one compound of formula (I) in an amount ranging from 0.001% to 10% of the total weight of the composition and, preferably, in an amount ranging from 0.01% to 5% of the total weight of the composition.

The subject compositions can be ingested, injected or topically applied to human skin (over any cutaneous region of the body), hair, nails or mucous membranes (buccal, jugal, gingival, genital or connective). Depending on the mode of administration, the compositions according to the invention can be provided in all of the pharmaceutical dosage forms conventional to this art.

For topical application onto the skin, the subject compositions can be formulated, in particular, as an aqueous or oily solution or as a dispersion of the lotion or serum type, as emulsions having a liquid or semi-liquid consistency of the milk type, obtained by dispersion of a fatty phase in an aqueous phase (O/W) or vice versa (W/O), or as suspensions or emulsions having a soft consistency of the aqueous or anhydrous gel or cream type, or, alternatively, as microcapsules or microparticles, or as vesicular dispersions of ionic and/or nonionic type. These compositions are formulated via conventional techniques.

The subject compositions can also be applied onto hair in the form of aqueous, alcoholic or aqueous/alcoholic solutions, or in the form of creams, gels, emulsions or foams, or, alternatively, in the form of aerosol compositions also comprising a pressurized propellant.

The compositions according to the invention can also be formulated as a hair care composition and, in particular, a shampoo, a hair setting lotion, a treating lotion, a styling cream or gel, a dyeing composition (in particular oxidation dyeing composition), optionally in the form of coloring shampoos, hair restructuring lotions, a permanent wave composition (in particular a composition for the first step of permanent waving), a lotion or gel for combating hair loss, an antiparasitic shampoo, and the like.

For injection, the subject compositions can be provided in the form of an aqueous or oily lotion or in the form of a serum. For the eyes, they can be provided in the form of drops and, for ingestion, they can be provided in the form of capsules, granules, syrups or tablets.

The amounts of the various constituents of the compositions according to the invention are those conventionally formulated in the fields under consideration.

The compositions according to the invention can also be provided as solid preparations constituting cleansing soaps or bars.

The subject compositions can also be packaged in the form of an aerosol composition also comprising a pressurized propellant.

When the composition is an emulsion, the proportion of the fatty phase advantageously ranges from 5% to 80% by weight and preferably from 5% to 50% by weight with respect to the total weight of the composition. The oils, waxes, emulsifiers and coemulsifiers comprising the composition in the form of an emulsion are selected from among those conventionally employed in the cosmetics field. The emulsifier and the coemulsifier are typically present in the composition in a proportion ranging from 0.3% to 30% by weight and preferably from 0.5% to 20% by weight with respect to the total weight of the composition. In addition, the emulsion can comprise lipid vesicles.

When the composition is an oily solution or gel, the fatty phase can constitute more than 90% of the total weight of the composition.

In known fashion, the subject cosmetic compositions can also comprise additives and adjuvants conventional in the cosmetics field, such as hydrophilic or lipophilic gelling agents, hydrophilic or lipophilic additives, preservatives, antioxidizing agents, solvents, fragrances, fillers, screening agents, odor absorbers and colorants. The amounts of these various additives and adjuvants are those conventionally employed in the cosmetic field and, for example, range from 0.01% to 10% of the total weight of the composition. These additives and adjuvants, depending on their nature, can be formulated into the fatty phase, into the aqueous phase and/or into the lipid spherules.

Exemplary oils or waxes which can be formulated into the compositions of the invention include the mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Exemplary emulsifiers according to the invention include glycerol stearate, polysorbate 60 and the PEG-6/PEG-32/Glycol Stearate mixture marketed under the trademark Tefose® 63 by Gattefosse.

Exemplary solvents according to the invention include the lower alcohols, in particular ethanol and isopropanol, or propylene glycol.

And exemplary hydrophilic gelling agents according to the invention include carboxyvinyl polymers (carbomer), acrylic copolymers, such as acrylate/alkyl acrylate copolymers, polyacrylamides, polysaccharides, such as hydroxypropylcellulose, natural gums and clays and exemplary lipophilic gelling agents include modified clays, such as bentones, metal salts of fatty acids, such as aluminum stearates, and hydrophobic silica, ethylcellulose or polyethylene.

The subject compositions can also comprise other hydrophilic active agents and principles, such as proteins or protein hydrolysates, amino acids, polyols, urea, allantoin, sugars and sugar derivatives, water-soluble vitamins, plant extracts, hydroxyacids, etc.

Exemplary lipophilic active principles include retinol (vitamin A) and derivatives thereof, tocopherol (vitamin E) and its derivatives, essential fatty acids, ceramides, essential oils, or salicylic acid and derivatives thereof.

According to the present invention, the subject compositions may contain at least one compound of formula (I) and at least one other active agent or principle. Representative such active agents/principles are:

(a) agents which improve the activity with respect to hair regrowth and/or with respect to retarding hair loss and which are already known for this activity, such as, for example, nicotinic acid esters, including, in particular, tocopherol nicotinate, benzyl nicotinate and nicotinates of $C_1$–$C_6$ alkyls, such as methyl or hexyl nicotinates, pyrimidine derivatives, such as 2,4-diamino-6-piperidinopyrimidine 3-oxide or "Minoxidil", disclosed in U.S. Pat. Nos. 4,139,619 and 4,596,812, or agents which promote hair regrowth, such as those described in the European patent application published under the number 0,648,488 and assigned to the assignee hereof;

(b) agents which decrease cutaneous pigmentation and/or proliferation and/or differentiation, such as retinoic acid and isomers thereof, retinol and esters thereof, vitamin D and derivatives thereof, estrogens, such as estradiol, kojic acid or hydroquinone;

(c) antibacterials, such as clindamycin phosphate, erythromycin or antibiotics from the tetracycline class;

(d) agents for combating parasites, in particular metronidazole, crotamiton or pyrethroids;

(e) antifungals, in particular compounds belonging to the imidazole class, such as econazole, ketoconazole or miconazole or salts thereof, polyene compounds, such as amphotericin B, compounds of the allylamine family, such as terbinafine, or, alternatively, octopirox;

(f) antiviral agents, such as acyclovir;

(g) steroidal anti-inflammatory agents, such as hydrocortisone, betamethasone valerate or clobetasol propionate, or nonsteroidal anti-inflammatory agents, such as, for example, ibuprofen and salts thereof, diclofenac and salts thereof, acetylsalicylic acid, acetaminophen or glycyrrhizic acid;

(h) anaesthetic agents, such as lidocaine hydrochloride and derivatives thereof;

(i) antipruriginous agents, such as thenaldine, trimeprazine or cyproheptadine;

(j) keratolytic agents, such as α- and β-hydroxycarboxylic acids or β-ketocarboxylic acids, their salts, amides or esters and more particularly hydroxyacids, such as glycolic acid, lactic acid, salicylic acid, citric acid and generally fruit acids, and 5-(n-octanoyl)salicylic acid;

(k) agents for combating or scavenging free radicals, such as α-tocopherol and esters thereof, superoxide dismutases, certain metal chelating agents or ascorbic acid and esters thereof;

(l) antiseborrhoeics, such as progesterone;

(m) antidandruff agents, such as octopirox or zinc pyrithione;

(n) antiacne agents, such as retinoic acid or benzoyl peroxide, (o) extracts of plant or bacterial origin.

Other active agents/principles can also be included, for example diazoxide, spiroxazone, phospholipids, such as lecithin, linoleic and linolenic acids, salicylic acid and derivatives thereof described in FR-2,581,542, such as salicylic acid derivatives bearing an alkanoyl group having from 2 to 12 carbon atoms in the 5-position of the benzene ring, hydroxycarboxylic or ketocarboxylic acids and esters thereof, lactones and their corresponding salts, anthralin, carotenoids, eicosatetrayenoic and eicosatriyenoic acids or their esters and amides, vitamin D and derivatives thereof, or extracts of plant or bacterial origin.

Thus, in one embodiment, the compositions according to the invention also comprise at least one agent selected from among antibacterial agents, agents for combating parasites, antifungals, antivirals, anti-inflammatories, antipruritics, anaesthetics, keratolytics, agents for combating free radicals, antiseborrhoeics, antidandruff agents, antiacne agents and/or agents which decrease cutaneous pigmentation and/or proliferation and/or differentiation, or extracts of plant or bacterial origin.

The subject compositions may also comprise at least one compound as indicated above that is in the liposomed form, such as described in WO-94/22468, filed Oct. 13, 1994, by Anti-Cancer Inc. The compound encapsulated in the liposomes can thus be delivered selectively to hair follicles.

The pharmaceutical compositions according to the invention can be administered parenterally, enterally or topically. Such pharmaceutical compositions are preferably administered topically.

The present invention thus features formulating, into cosmetic/pharmaceutical compositions comprising a physiologically acceptable medium therefor (vehicle, diluent or carrier), an effective amount of at least one compound of above formula (I).

This because the compounds of formula (I) are excellent potassium channel openers, the principal property of Minoxidil, the only compound currently recognized as effective in treatments for hair loss.

They are also excellent antagonists of androgen receptors, androgens being responsible for a particularly widespread form of alopecia, androgen-dependent alopecia. However, it is also known that androgens are implicated in hyperseborrhoea and acne.

Thus, the compounds of formula (I) exhibit notable activities which justify their use as medicaments, in particular for inducing and/or stimulating hair growth and/or retarding hair loss and/or for the treatment of hyperseborrhoea and/or acne.

To date, N-aryl-2-hydroxyalkylamide compounds having mixed potassium channel opener/antiandrogen activity have not been employed for combating hair loss and/or for treating hyperseborrhoea and/or acne.

Accordingly, this invention also features formulating an effective active principle amount of at least one compound of formula (I) into cosmetic/pharmaceutical compositions well suited to induce and/or stimulate hair growth and/or retard hair loss and/or to treat hyperseborrhoea and/or acne.

Of course, the subject compounds can be used either alone or as a mixture.

The cosmetic compositions according to the invention are topically applied to the regions of the body requiring such treatment, such as, for example, the alopecic regions of the scalp or hair of an individual. The cosmetic compositions can then optionally be maintained in contact with the skin/hair/scalp for several hours and then optionally rinsed therefrom. It is possible, for example, to topically apply a composition comprising an effective active principle amount of at least one compound as indicated above in the evening, to maintain the composition in contact with the skin/hair/scalp overnight and optionally to shampoo it therefrom in the morning. These applications can be repeated daily over one or more months, depending on the particular individual.

The present invention thus also features a regime or regimen for cosmetically treating the hair and/or scalp and/or skin, comprising topically applying, to the hair and/or scalp and/or skin, a cosmetic composition comprising an effective active principle amount of at least one compound of formula (I), maintaining such composition in contact with the hair and/or scalp and/or skin, and, optionally, rinsing same therefrom.

Such regime/regimen presents the characteristics of a cosmetic treatment insofar as it permits the appearance of the hair and/or skin to be improved by imparting a greater strength and an improved appearance thereto.

In order to further illustrate the present invention and the advantages thereof, the following specific examples are given, it being understood that same are intended only as illustrative and in nowise limitative.

EXAMPLE 1

Synthesis of the Ethyl Ester of (4-Cyano-3-(trifluoromethyl)phenyl)(3,3,3-trifluoro-2-hydroxy-2-methylpropionyl)carbamic Acid Having the Formula:

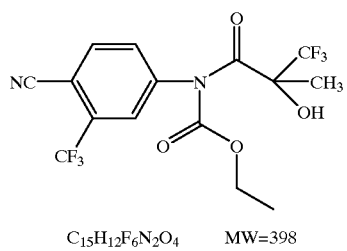

$C_{15}H_{12}F_6N_2O_4$    MW=398

(a) Preparation of 4-(5-methyl-2,4-dioxo-5-(trifluoromethyl)oxazolidin-3-yl)-2-(trifluoromethyl)-benzonitrile:

1.09 g of 4-isocyanato-2-(trifluoromethyl)-benzonitrile were dissolved in 20 ml of anhydrous THF. 150 μl of triethylamine were added, followed by 860 mg of trifluoroacetone cyanohydrin in solution in 10 ml of anhydrous THF. The reaction mixture was stirred at room temperature for 2 hours (h).

5 ml of methanol were added, followed, after 30 min, by 10 ml of 1 N hydrochloric acid. After 2 h at room temperature, 20 ml of water were added. The reaction mixture was extracted with 4×25 ml of dichloromethane. The organic phase was washed with 25 ml of water, dried over sodium sulfate and evaporated to dryness. The residue obtained was purified by chromatography on a silica column, the eluent being dichloromethane. 540 mg of a white precipitate were obtained.

(b) Synthesis of the Ethyl Ester of (4-Cyano-3-(trifluoromethyl)phenyl)(3,3,3-trifluoro-2-hydroxy-2-methylpropionyl)carbamic Acid:

4.3 g of 4-(5-methyl-2,4-dioxo-5-(trifluoromethyl)oxazolidin-3-yl)-2-(trifluoromethyl)benzonitrile were dissolved in 50 ml of ethanol. The solution was heated to reflux for 7 days and then evaporated to dryness. The residue was purified by chromatography on a silica column (eluent: dichloromethane) and then recrystallized from a 2/1 heptane/toluene mixture.

1.4 g of ethyl ester of (4-cyano-3-(trifluoromethyl)phenyl)(3,3,3-trifluoro-2-hydroxy-2-methylpropionyl) carbamic acid was obtained, for a yield of 29%.

Analyses:
$^1$H NMR (in CD$_3$CN): δ (ppm)=1.23 (t, 3H), 1.87 (d, 3H), 4.27 (q, 2H), 7.75 (dd, 1H), 7.88 (d, 1H), 7.94 (d, 1H), 8.93 (s, 1H)
$^{13}$C NMR (in CD$_3$CN): δ (ppm)=14.14, 17.51, 64.17, 81.06, 104.26, 116.66, 117.34, 123.60, 123.99, 134.12, 137.38, 143.66, 151.49, 165.97

Elemental analysis:

|  | C | H | N | F |
|---|---|---|---|---|
| % Calculated | 45.23 | 3.01 | 7.03 | 28.64 |
| % Found | 45.21 | 3.09 | 6.86 | 28.48 |

EXAMPLE 2

Synthesis of (4-Cyano-3-(trifluoromethyl)phenyl)(3,3,3-trifluoro-2-hydroxy-2-methylpropionyl)carbamic Acid Having the Formula:

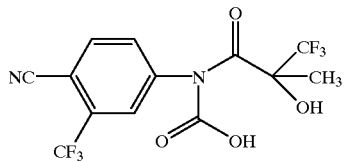

C$_{13}$H$_8$F$_6$N$_2$O$_4$    MW=370

100 mg of 4-(5-methyl-2,4-dioxo-5-(trifluoromethyl)oxazolidin-3-yl)-2-(trifluoromethyl)-benzonitrile, as prepared in Example 1, were dissolved in 20 ml of a 7/3 ethanol/water mixture and stirred for 5 days at room temperature. The reaction mixture was evaporated to dryness and then purified by chromatography on an RP18 silica column (eluent: 6/4 water/acetonitrile). 18 mg of (4-cyano-3-(trifluoromethyl)phenyl)(3,3,3-trifluoro-2-hydroxy-2-methylpropionyl)carbamic acid were obtained, for a yield of 17%.

Analyses:
$^1$H NMR (in CD$_3$CN): δ (ppm)=1.86 (s, 3H), 7.75 (dd, 1H), 7.86 (d, 1H), 7.95 (d, 1H), 8.75 (s, 1H)
$^1$H NMR (in d$_6$-DMSO): δ (ppm)=1.81 (s, 3H), 7.84 (dd, 1H), 8.08 (d, 1H), 8.10 (d, 1H), 10.88 (s, 1H), 14.36 (s, OH)
$^{13}$C NMR (in CD$_3$CN): δ (ppm)=16.36, 104.15, 116.68, 117.28, 122.36, 134.12, 137.54, 143.72, 151.52, 166.97
$^{19}$F NMR (in CD$_3$CN): δ (ppm)=−61.00 (CF$_3$), −77.12 (F11)

EXAMPLE 3

Synthesis of 1-(3,4-Dichlorophenyl)-3-propyl-1-(3,3,3-trifluoro-2-hydroxy-2-methylpropionyl)urea Having the Formula:

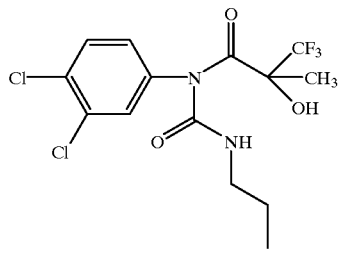

C$_{14}$H$_{15}$Cl$_2$F$_3$N$_2$O$_3$    MW=387

(a) Preparation of 3-(3,4-Dichlorophenyl)-5-methyl-5-(trifluoromethyl)oxazolidine-2,4-dione:

3 g of N-(3,4-dichlorophenyl)-3,3,3-trifluoro-2-hydroxy-2-methylpropionamide were dissolved in 50 ml of THF distilled beforehand over sodium/benzophenone. 1 g of sodium hydride (NaH), at 60% in oil, was added. The reaction mixture was stirred for 30 min and then cooled to 0–5°. 2.3 g of ethyl chloroformate, in solution in 10 ml of THF, were added without exceeding 5° C. After maintaining overnight at room temperature, the reaction mixture was poured onto 100 ml of ice-cold water and then extracted with 4×50 ml of dichloromethane. The organic phase was washed with 20% sodium chloride, dried over sodium sulfate and evaporated to dryness. The residue was purified by silica chromatography (eluent: 1/1 heptane/dichloromethane). 1.25 g of 3-(3,4-dichlorophenyl)-5-methyl-5-(trifluoromethyl)oxazolidine-2,4-dione was obtained, for a yield 38%.

Analyses:
$^1$H NMR (in d$_6$-DMSO): δ (ppm)=1.96 (s, 3H) 7.57 (dd, 1H), 7.88 (d, 1H), 7.90 (d, 1H)
$^{13}$C NMR (in d$_6$-DMSO): δ (ppm)=15.05, 81.84, 121.49, 126.78, 128.35, 129.75, 131.35, 131.62, 132.46, 150.98, 165.95

Elemental Analysis:

|  | C | H | Cl | F | N |
|---|---|---|---|---|---|
| % Calculated | 40.24 | 1.83 | 21.65 | 17.38 | 4.27 |
| % Found | 40.29 | 1.96 | 21.70 | 17.48 | 4.35 |

(b) Synthesis of 1-(3,4-Dichlorophenyl)-3-propyl-1-(3,3,3-trifluoro-2-hydroxy-2-methylpropionyl)urea:

200 mg of 3-(3,4-dichlorophenyl)-5-methyl-5-(trifluoromethyl)oxazolidine-2,4-dione were dissolved in 10 ml of dichloromethane. 55 μl of propylamine were added. The reaction mixture was stirred for 24 hours at room temperature. After evaporation, the residue was purified by chromatography on a silica column (eluent: dichloromethane). 155 mg of 1-(3,4-dichlorophenyl)-3-propyl-1-(3,3,3-trifluoro-2-hydroxy-2-methylpropionyl) urea were obtained, for a yield of 63%.

Analyses:

$^1$H NMR (in d$_6$-DMSO): δ (ppm)=0.84 (t, 3H), 1.43 (m, 2H), 1.81 (s, 3H), 2.94 (m, 2H), 7.59 (d, 1H), 7.65 (dd, 1H), 7.69 (t, 1H), 7.95 (d, 1H), 10.17 (s, OH)

EXAMPLE 4

Measurement of the Affinity (IC$_{50}$) of the Ethyl Ester of (4-Cyano-3-(trifluoromethyl)phenyl)(3,3,3-trifluoro-2-hydroxy-2-methylpropionyl)carbamic Acid (Example 1) and of (4-Cyano-3-(trifluoromethyl)phenyl)(3,3,3-trifluoro-2-hydroxy-2-methylpropionyl)carbamic Acid (Example 2) for the Androgen Receptor:

These measurements of receptor affinity for the androgen receptor were carried out according to the technique of Schilling and Liao, described in *The Prostate*, 5, p. 581–588 (1984).

During the experimentation, the reference molecule (mibolerone) was tested in parallel at 8 concentrations, in order to validate the experiment.

TABLE I

| Example No. | Inhibition of the binding of testosterone: IC$_{50}$ (μM) |
| --- | --- |
| 1 | 2 |
| 2 | 4 |

The internal reference (mibolerone) inhibited the binding of testosterone to its receptor by 50% at a concentration of 4.3 nM.

EXAMPLE 6

Measurement of the Activity of "Potassium Channel Opener" Type of the Ethyl Ester of (4-Cyano-3-(trifluoromethyl)phenyl)(3,3,3-trifluoro-2-hydroxy-2-methylpropionyl)carbamic Acid (Example 1) and of (4-cyano-3-(trifluoromethyl)phenyl)(3,3,3-trifluoro-2-hydroxy-2-methylpropionyl)carbamic Acid (Example 2) by the in Vitro Measurement of the Relaxant Power of the Molecules on Rings of the Thoracic Region of the Aorta (IC$_{50}$):

The experiments were carried out according to the techniques of Newgreen et al. (*Br. J. Pharmacol.*, 100, p. 605–613 (1990)), Bray et al. (*Arch. Pharmacol.*, 344, p. 351–359 (1991)) and Wickerden et al. (*Br. J. Pharmacol.*, 103, 1148–1152 (1991)).

After they had been mounted into the isolated organ vessels, the tissues (aortic smooth muscles) were subjected to an initial tension of 2 g.

After an equilibration period, the tissues were exposed to a potassium chloride solution (20 mM KCl), in order to obtain a sustained contractile response.

After stabilization of this contractile response, the relaxant activity (of potassium channel opener type) of the test molecules was evaluated as a function of the concentration applied.

During the experimentation, two reference molecules were employed: cromakalim and minoxidil. They exhibited IC$_{50}$ values on the order of 1 μM.

TABLE II

| Example No. | Inhibition contraction isolated aorta induced by K$^+$: IC$_{50}$ (μM) |
| --- | --- |
| 1 | 2 |
| 2 | 3 |

These results indicate that the compounds of Examples 1 and 2 exhibit a mixed activity.

EXAMPLE 7

The following are specific examples of compositions according to the invention comprising the subject novel N-aryl-2-hydroxyalkylamide compounds.

These compositions were formulated via conventional techniques in the cosmetics and pharmaceuticals arts.

| Lotion for combating hair loss: | |
| --- | --- |
|  | 1.000 g |
| Compound of Example 3 | 30.000 g |
| Propylene glycol | 40.500 g |
| Ethyl alcohol | 100.000 g |
| Water | q.s. for |

This lotion was topically applied to the scalp, once or twice daily, in a proportion of 1 ml per application.

| Thickened lotion for combating hair loss: | |
| --- | --- |
|  | 0.500 g |
| Compound of Example 2 | 2.000 g |
| Kawain | 3.500 g |
| Hydroxypropylcellulose* | 100.000 g |
| Ethyl alcohol | q.s. for |

This thickened lotion was topically applied to the scalp, once or twice daily, in a proportion of 1 ml per application.

| Lotion for combating hair loss: | |
| --- | --- |
|  | 0.200 g |
| Compound of Example 1 | 20.000 g |
| Propylene glycol monomethyl ether** | 3.000 g |
| Hydroxypropylcellulose* | 40.000 g |
| Ethyl alcohol | 2.000 g |
| Minoxidil | 100.000 g |
| Water | q.s. for |

*Klucel G ® marketed by Hercules
**Dowanol PM ® marketed by Dow Chemical

This thickened lotion was topically applied to the scalp, once or twice daily, in a proportion of 1 ml per application.

| Lotion for combating hair loss: | |
| --- | --- |
|  | 0.100 g |
| Compound of Example 3 | 10.000 g |
| Propylene glycol | 100.000 g |
| Isopropyl alcohol | q.s. for |

1 ml of this lotion was topically applied to the scalp at the rate of once or twice daily.

A retarding in hair loss and/or a regrowth effect was observed, after several months of treatment and depending on the individual subject treated, with each of the compositions described in the above examples.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An N-aryl-2-hydroxyalkylamide compound having the structural formula (I):

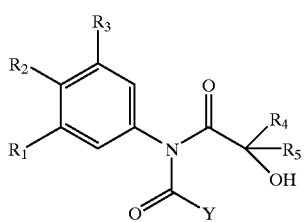

(I)

in which $R_1$ is a hydrogen atom, a halogen atom, a cyano group (—CN), a $C_1$–$C_4$ alkyl radical, a perfluoroalkyl radical or an —$OR_6$ radical, wherein $R_6$ is a hydrogen atom or a $C_1$–$C_4$ alkyl radical; $R_2$ is a nitro group (—$NO_2$), a cyano group (—CN), a halogen atom, an —$SO_2R_7$ radical, a —$COR_7$ radical or a —$COOR_7$ radical, wherein $R_7$ is a hydrogen atom, a $C_1$–$C_4$ alkyl radical or a phenyl radical optionally substituted by at least one halogen atom; $R_3$ is a hydrogen atom, a halogen atom, a cyano group (—CN), a $C_1$–$C_4$ alkyl radical optionally substituted by at least one halogen atom, or an —$OR_6$ radical, wherein $R_6$ is a hydrogen atom or a $C_1$–$C_4$ alkyl radical; $R_4$ is a hydrogen atom or a $C_1$–$C_4$ alkyl radical optionally substituted by at least one halogen atom; $R_5$ is a $C_1$–$C_4$ alkyl radical substituted by at least one halogen atom or a phenyl radical optionally substituted by at least one halogen atom, a cyano group (—CN) or a nitro group (—$NO_2$); Y is an —OR radical or an —NRR' radical; and R and R', which may be identical or different, are each a hydrogen atom, a $C_1$–$C_8$ alkyl radical optionally substituted by at least one hydroxyl radical (—OH), or a —$COOR_6$ radical; with the proviso that, when Y is —NRR', R and R', together with the nitrogen atom from which they depend, can form a 5- or 6-membered heterocyclic ring member; or isomer, acylated derivative or pharmaceutically acceptable salt thereof.

2. The N-aryl-2-hydroxyalkylamide compound as defined by claim 1, wherein formula (I), $R_1$ is a halogen atom.

3. The N-aryl-2-hydroxyalkylamide compound as defined by claim 1, wherein formula (I), $R_1$ is a $C_1$–$C_4$ alkyl radical.

4. The N-aryl-2-hydroxyalkylamide compound as defined by claim 1, wherein formula (I), $R_1$ is a perfluoroalkyl radical.

5. The N-aryl-2-hydroxyalkylamide compound as defined by claim 1, wherein formula (I), $R_1$ is an —$OR_6$ radical.

6. The N-aryl-2-hydroxyalkylamide compound as defined by claim 1, wherein formula (I), $R_2$ is a halogen atom.

7. The N-aryl-2-hydroxyalkylamide compound as defined by claim 1, wherein formula (I), $R_2$ is an —$SO_2$—$R_7$ radical.

8. The N-aryl-2-hydroxyalkylamide compound as defined by claim 1, wherein formula (I), $R_2$ is a —$COR_7$ radical.

9. The N-aryl-2-hydroxyalkylamide compound as defined by claim 1, wherein formula (I), $R_2$ is a —$COOR_7$ radical.

10. The N-aryl-2-hydroxyalkylamide compound as defined by claim 1, wherein formula (I), $R_3$ is a halogen atom.

11. The N-aryl-2-hydroxyalkylamide compound as defined by claim 1, wherein formula (I), $R_3$ is a $C_1$–$C_4$ alkyl radical optionally substituted by at least one halogen atom.

12. The N-aryl-2-hydroxyalkylamide compound as defined by claim 1, wherein formula (I), $R_3$ is an —$OR_6$ radical.

13. The N-aryl-2-hydroxyalkylamide compound as defined by claim 1, wherein formula (I), $R_4$ is a $C_1$–$C_4$ alkyl radical.

14. The N-aryl-2-hydroxyalkylamide compound as defined by claim 1, wherein formula (I), $R_4$ is a $C_1$–$C_4$ alkyl radical substituted by at least one halogen atom.

15. The N-aryl-2-hydroxyalkylamide compound as defined by claim 1, wherein formula (I), $R_5$ is a $C_1$–$C_4$ alkyl radical substituted by at least one halogen atom.

16. The N-aryl-2-hydroxyalkylamide compound as defined by claim 1, wherein formula (I), $R_4$ and $R_5$ are different.

17. The N-aryl-2-hydroxyalkylamide compound as defined by claim 1, wherein formula (I), Y is an —NHR radical.

18. The N-aryl-2-hydroxyalkylamide compound as defined by claim 1, wherein formula (I), R is a $C_1$–$C_8$ alkyl radical.

19. The N-aryl-2-hydroxyalkylamide compound as defined by claim 1, wherein formula (I), R is a —$COOR_6$ radical.

20. The N-aryl-2-hydroxyalkylamide compound as defined by claim 1: (4-cyano-3-(trifluoromethyl)phenyl)(3,3,3-trifluoro-2-hydroxy-2-methylpropionyl)carbamic acid.

21. The N-aryl-2-hydroxyalkylamide compound as defined by claim 1: the ethyl ester of (4-cyano-3-(trifluoromethyl)phenyl)(3,3,3-trifluoro-2-hydroxy-2-methylpropionyl)carbamic acid.

22. The N-aryl-2-hydroxyalkylamide compound as defined by claim 1: 1-(3,4-dichlorophenyl)-3-propyl-1-(3,3,3-trifluoro-2-hydroxy-2-methylpropionyl)urea.

23. The N-aryl-2-hydroxyalkylamide compound as defined by claim 1: 1-(3,4-dichlorophenyl)-3-benzyl-1-(3,3,3-trifluoro-2-hydroxy-2-methylpropionyl)urea.

24. The N-aryl-2-hydroxyalkylamide compound as defined by claim 1: 1-(3,4-dichlorophenyl)-3-piperidinyl-1-(3,3,3-trifluoro-2-hydroxy-2-methylpropionyl)urea.

25. The N-aryl-2-hydroxyalkylamide compound as defined by claim 1: 1-(4-sulfonylphenyl)-3-propyl-1-(3,3,3-trifluoro-2-hydroxy-2-methylpropionyl)urea.

26. The N-aryl-2-hydroxyalkylamide compound as defined by claim 1: 1-(4-benzoylphenyl)-3-propyl-1-(3,3,3-trifluoro-2-hydroxy-2-methylpropionyl)urea.

27. The N-aryl-2-hydroxyalkylamide compound as defined by claim 1: the ethyl ester of (3,4-dichlorophenyl) (3,3,3-trifluoro-2-hydroxy-2-methylpropionyl)carbamic acid.

28. The N-aryl-2-hydroxyalkylamide compound as defined by claim 1: 1-(3,4-dichlorophenyl)-3-(4-hydroxybutyl)-(3,3,3-trifluoro-2-hydroxy-2-methylpropionyl) urea.

29. A cosmetic/pharmaceutical composition suited for inducing/stimulating hair growth and/or retarding hair loss and/or for treating hyperseborrhea and/or acne, comprising an amount effective to elicit at least one of the following activities: (i) inducing or stimulating hair growth; (ii) retarding hair loss; (iii) treating hyperseborrhea and (iv) treating acne, of at least one N-aryl-2-hydroxyalkylamide compound as defined by claim 1, formulated into a cosmetically/pharmaceutically acceptable vehicle, diluent or carrier therefor.

30. The cosmetic/pharmaceutical composition as defined by claim 29, comprising from 0.0001% to 5% by weight of said at least one N-aryl-2-hydroxyalkylamide compound.

31. The cosmetic/pharmaceutical composition as defined by claim 29, comprising from 0.001% to 2% by weight of said at least one N-aryl-2-hydroxyalkylamide compound.

32. The cosmetic/pharmaceutical composition as defined by claim 29, comprising from 0.001% to 10% by weight of said at least one N-aryl-2-hydroxyalkylamide compound.

33. The cosmetic/pharmaceutical composition as defined by claim 29, comprising from 0.01% to 5% by weight of said at least one N-aryl-2-hydroxyalkylamide compound.

34. The cosmetic/pharmaceutical composition as defined by claim 29, further comprising an effective amount of at least one active agent selected from among antibacterial agents, agents for combating parasites, antifungals, antivirals, anti-inflammatories, antipruritics, anaesthetics, keratolytics, agents for combating free radicals, antiseborrhoeics, antidandruff agents, antiacne agents, agents which decrease cutaneous pigmentation and/or proliferation and/or differentiation, extracts of plant or bacterial origin, or combination thereof.

35. The cosmetic/pharmaceutical composition as defined by claim 29, formulated for topical application onto the skin, hair and/or scalp of a human subject.

36. The cosmetic/pharmaceutical composition as defined by claim 29, formulated for injection into a human subject.

37. The cosmetic/pharmaceutical composition as defined by claim 29, formulated for ingestion by a human subject.

38. The cosmetic/pharmaceutical composition as defined by claim 29, comprising a solution, dispersion, emulsion, gel, cream, milk, serum, foam, aerosol, lotion, dye composition, shampoo, eyedrops, syrup, capsules, granules, tablets, soap, microcapsules, microparticles, or vesicular dispersion.

39. The cosmetic/pharmaceutical composition as defined by claim 29, further comprising an effective amount of an auxiliary active agent also suited for inducing/stimulating hair growth and/or retarding hair loss.

40. A regime or regimen for inducing/stimulating hair growth and/or retarding hair loss on a human subject in need of such treatment, comprising administering to said human subject an effective amount of the cosmetic/pharmaceutical composition as defined by claim 29, for a period of time sufficient to elicit said hair growth-/hair loss-affecting response.

41. A regime or regimen for therapeutically treating hyperseborrhea and/or acne afflicting a human subject, comprising administering to said human subject an effective amount of the cosmetic/pharmaceutical composition as defined by claim 29, for a period of time sufficient to elicit said hyperseborrhea-/acne-affecting response.

42. A process for the preparation of the N-aryl-2-hydroxyalkylamide compound as defined by claim 1, comprising first reacting an isocyanate with a cyanohydrin in the presence of an amine, then treating the mixture of reaction with hydrochloric acid, next adding an excess of alcohol or amine to a solution of the N-aryl-2,4-dioxooxazolidine thus formed, and thence heating such mixture for such period of time as to convert same into said N-aryl-2-hydroxyalkylamide compound.

* * * * *